(12) United States Patent  
Talley et al.

(10) Patent No.: US 7,878,042 B2
(45) Date of Patent: Feb. 1, 2011

(54) SHOCK SIMULATION GENERATOR (75) Inventors: Michael A. Talley, Suffolk, VA (US);
Charles L. Pizzano, Norwood, MA (US); Carla J. Davis, Hampton, VA (US); Jonathan R. Harn, Newport News, VA (US)

(73) Assignee: Newport News Shipbuilding and Dry Dock Company, Los Angeles, CA (US)

( * ) Notice: Subject to any disclaimer, the term of this patent is extended or adjusted under 35 U.S.C. 154(b) by 75 days.

(21) Appl. No.: 12/248,749

(22) Filed: Oct. 9, 2008

(65) Prior Publication Data

US 2009/0090166 A1 Apr. 9, 2009

Related U.S. Application Data

(60) Provisional application No. 60/978,433, filed on Oct. 9, 2007.

(51) Int. Cl.
*G01N 3/30* (2006.01)
(52) U.S. Cl. ..................................... 73/12.06; 73/12.13
(58) Field of Classification Search ...... 73/12.06–12.13
See application file for complete search history.

(56) References Cited

U.S. PATENT DOCUMENTS

| | | | | |
|---|---|---|---|---|
| 4,509,362 | A * | 4/1985 | Lyons | 73/79 |
| 6,684,681 | B1 * | 2/2004 | Zombo | 73/12.11 |
| 7,111,492 | B2 * | 9/2006 | Paitich | 73/12.02 |
| 2005/0044927 | A1 * | 3/2005 | Paitich | 73/12.09 |
| 2007/0200715 | A1 * | 8/2007 | Durand | 340/573.6 |

OTHER PUBLICATIONS

MIL-S-901D (Navy) Military Specification; *Requirements for Shock Tests, H.I. (High-Impact) Shipboard Machinery, Equipment, and Systems*; Mar. 17, 1989.
Michael A. Talley and Shahram Sarkani; *A New Simulation Method Providing Shock Mount Selection Assurance*; 2003; pp. 231-267; EBSCO Publishing.
*CNC Plasma Cutting System*; available at <http://www.roymech.co.uk/Useful_Tables/Mechanics/Linkages.html> (visited Oct. 2, 2008).
Mike Campbell; *Subsidiary Component Shock Qualification Testing; Current Navy Process, Criteria, and Testing* (Abstract); 75th Shock & Vibration Symposium, Virginia Beach, Virginia; Oct. 17-22, 2004; 2 pages; Shock and Vibration Information Analysis Center.
David Callahan, Michael Talley, Kevin Gould, Dave Vogel; *Investigation of Loading Effects on Deck Simulator Fixtures Used in MIL-S-901D Heavyweight Testing* (Abstract); 77th Shock and Vibration Symposium, Monterey, California; Oct. 29-Nov. 2, 2006; 2 pages; Shock and Vibration Information Analysis Center.
Charles Pizzano, Michael Talley, Steve Borgman, Calvin Milam; *Barge Environmental Shock Test (BEST) Machine* (Abstract); 77th Shock and Vibration Symposium, Monterey, California; Oct. 29-Nov. 2, 2006; 2 pages; Shock and Vibration Information Analysis Center.

* cited by examiner

*Primary Examiner*—Max Noori
(74) *Attorney, Agent, or Firm*—Alston & Bird LLP (57) ABSTRACT

This is directed to systems, methods, computer programs and other means for shock testing a piece of equipment, i.e., the target. The target can be mounted to a shock generation machine, which is then slammed into a sturdy foundation. The impact can result in multi-axis loads, depending on how the machine is configured, while also simulating the modal frequency response of an object, such as a naval ship's deck.

28 Claims, 11 Drawing Sheets

SHOCK SIMULATION GENERATOR

CROSS-REFERENCE TO RELATED APPLICATIONS

This application is related to and claims the benefit of U.S. Provisional Patent Application No. 60/978,433 ("the '433 Prov. App."), filed Oct. 9, 2007, which is incorporated herein by reference in its entirety.

TECHNICAL FIELD

This relates to systems, methods and other means for generating shocks. In some embodiments, the shocks simulate a sudden and violent blow or impact that a component may experience on a naval warship or other platform.

BACKGROUND OF THE INVENTION

The United States military currently requires vigorous testing for any piece of equipment that is intended for battle. In some instances, even the components of some equipment, such as mission critical equipment, must be individually tested.

Shock testing is one type of testing used by the military and military contractors. Shock testing is meant to simulate an attack, such as an explosion from a bomb, torpedo or missile that occurs in close proximity to the device or component. Electrical devices and components, such as circuit boards, sensors and routers, are often put through rigorous shock tests before the U.S. military will authorize their use in or for battle.

Shock testing helps ensure that mission critical components will not fail as a result of an explosion and/or other type of physical shock. These components are needed by military personal to continue to function properly during an attack. Accordingly, it is important that the shock testing of a component accurately simulate the type of shock(s) the component is likely to experience in battle.

Many U.S. Navy shock tests, for example, are currently administered by putting a device or component (sometimes referred to herein as a "shock test target" or "target") on a barge or platform that is in water (such as a large lake or pond). The barge can be engineered to simulate the reverberation frequency or frequencies of a specific boat, ship or part of a ship, such as a ship's deck. Explosives are placed in the water under the barge, and ignited. The subsequent explosion creates a wave of energy and an air bubble, both of which can shock the target. Although different targets may have to meet different standards, many shock test targets pass a particular shock test if the target is not damaged too badly as a result of the shock and/or still functions properly after the shock.

The shock created by an explosion or other attack can be broken down into different phases. The first phase is the initial shock, which is caused by energy from an explosion and/or physical impact of, for example, a missile or bomb. That energy can travel as a shock wave. A bubble is also created when the initial shock is the result of an under water explosion. The bubble usually follows the path of the initial shock wave. Accordingly, both the initial shockwave and the bubble will impact physical media they encounter, and each can create shock waves that propagate through the media (such as the ship's deck). Subsequent shock waves are the result of the energy from the initial shock being distributed and reverberating through the media.

Different substances and combinations of substances will react to different types and magnitudes of shock waves. An explosion directed at the side of a surface ship, for example, is likely to also cause the ship to rock side to side, thereby creating rotational and athwartship forces, while many of its components (such as its deck) reverberate at a specific frequency from the shock waves. Each shock wave can also cause one or more secondary shocks to a component. For example, when a torpedo explodes under water in close proximity to a side of a boat, the explosion creates an initial shock and a bubble, which travel through the water and each impact the hull of the boat. The boat's hull will then absorb at least some of the energy from the shock wave and the bubble, and rock side to side while reverberating at a particular frequency. If the explosion is great enough, the wave of energy can even blast a hole through the hull and/or the bubble can physically lift the hull of the boat out of the water, only to have it crash down into the water and break. Regardless of whether the hull withstands the initial shock wave and bubble, each reverberation can create its own mini-shock that can causes damage to equipment and injury to people on the boat. In addition, the reverberations can act collectively at a given frequency and cause even more damage. Eventually, the energy of the shock waves dissipates and can no longer be felt. A number of factors can influence how long it takes for the shock waves' energy to dissipate, many of which need to be considered when preparing to shock test the target.

Shock tests in many ways are controlled chaos, especially the heavy weight, high explosive tests that are currently conducted. Factors, such as the positioning of the target, power of the shock, direction of the shock and reverberation of the barge, are controlled and calculated to achieve a specific objective. Accordingly, a single target or type of target may have to be tested a number of times. Each explosive shock test can cost tens of thousands of dollars, but such tests are required nonetheless by the U.S. military.

BRIEF SUMMARY OF THE INVENTION

Methods, systems and other means are provided for impact shock testing. In accordance with some embodiments, a shock generation system can utilize a cage configured to receive a target device that is to be shock tested. The target device (sometimes referred to herein as "the target" or "the shock test target") can be any type of equipment, such as Class I equipment or Class II equipment, component or device.

The shock generation system can also comprise at least one swing arm coupled to the cage and a foundation. In some embodiments, the swing arms collectively form a four-bar link system with the foundation. Each swing arm, with the assistance of a corresponding hinging assembly, allows the cage to be moved, or swung, in one or more directions. For example, the cage can be hoisted up by a forklift or crane to a predetermined height, and then allowed to fall onto the foundation. When the swing arms are in the upwards position, the foundation can also support the weight of the cage, swing arms, target device, any extra weight, etc.

A resonation simulator can be located between the cage and foundation (e.g., bolted to the bottom of the cage). The resonation simulator can be, for example, a tunable spring coil apparatus or one or more high pressure air cylinders. The resonation simulator can be interchangeable and used to simulate any object's (including a ship deck's) modal frequency response to a shock, such as the type of shock that occurs in response to a close proximity explosion.

To prevent any unwanted rebounding response and to direct the shock energy at the target, the shock generation system can also include a locking assembly that quickly couples the cage to the foundation at impact. For example, the locking assembly can include two rotating forks that are integrated into the foundation and two locking pins in the resonation simulator. When the resonation simulator slams into the foundation, the locking pins enter the rotating forks, which prevent the cage from bouncing up. In other embodiments, the locking pin(s) or the locking assembly can be integrated into the cage, and/or an entirely different type of locking assembly can be used by the shock generation system.

The hinging mechanism that allows the cage to swing, can be any type of hinging mechanism. In some embodiments the hinging mechanism can allow the cage (and target) to fall in a manner that, upon impact, causes them to experience multi-axis loadings. For example, one or more adjustable devises can be used to cause the cage to fall at an angle that causes the target to experience athwartship and/or rotational acceleration forces upon impact.

One or more sensors can also be included in the shock generation system. The sensors can be, for example, accelerometers or other components that monitor and record the various velocities, forces, etc. experienced before, during and after the impact.

Although described above in the context of a shock generation system, other aspects of the present invention may provide for a corresponding method or methods for impact shock testing.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Traditional shock tests, which may use advanced pyrotechnics in remote regions of the country, can currently cost tens of thousands of dollars. In addition to the expensive materials used to blow-up the targets, engineers often spend hours, even weeks, preparing for a single set of explosive shock tests. Among other things, engineers must calculate the explosive force, angle, and direction used to create the shock. The engineers must also take into consideration the shock waves produced by the initial shock and under water bubble.

But even before the explosive test can be conducted, the target must be physically shipped to the test location. Simply getting a piece of sensitive military equipment to a remote test site can also be expensive. U.S. Navy ships, for example, are often built near the ocean, which are generally the most heavily populated locations in the country. Such populated locations often restrict the types of explosions that may be employed to conduct an explosive shock test. For this reason, most explosive shock tests are conducted in remote areas of the country in large lakes and ponds, where the risk to civilians is minimal and a number of simultaneous forces can be applied to a shock test target. As such, the shock test targets must be shipped, trucked and/or flown to these locations— just to be blown up.

Although there may be a number of ways to solve many of the problems associated with heavyweight, high explosive shock testing, embodiments of the present invention are focused on systems, methods and other means of using physical impact shock testing. By removing the explosive component of legacy shock tests, thousands, if not hundreds of thousands of dollars can be saved. But physical shock testing comes with a number of its own problems. For example, engineers must be able to control, simulate and/or monitor many variables, such as the force and direction of the initial shock, force of the bubble and a resonating frequency of a ship's deck. For at least this reason, tens of thousands of dollars are often spent to conduct explosive shock tests with, for example, a barge constructed out of the same materials as a real ship's deck in a remote lake.

Embodiments of the present invention overcome many of these obstacles (associated with traditional explosive shock testing as well as other types of physical shock testing) and now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
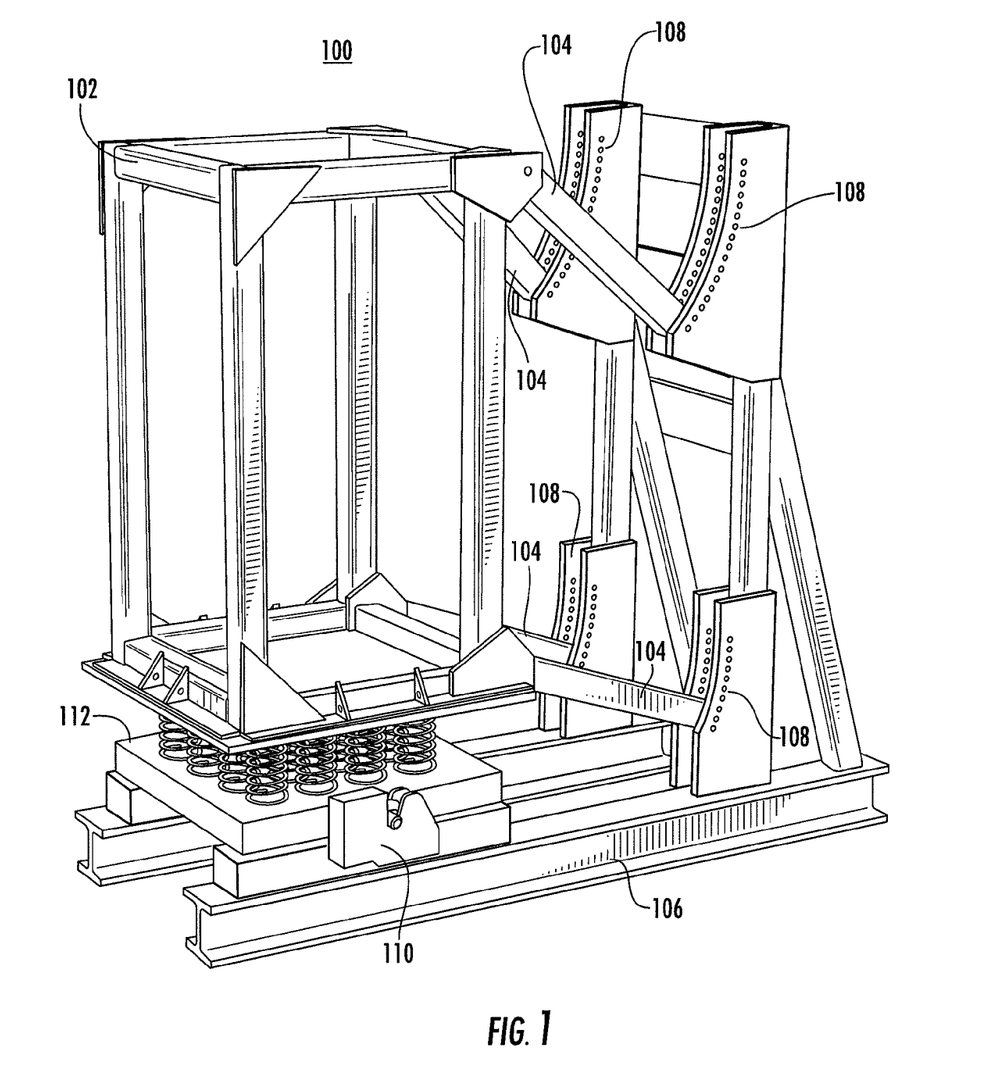
FIG. 1 is an exemplary illustration of a shock generation system in accordance with some embodiments of the present invention.

FIG. 1 shows shock generation system 100. Shock generation system 100 can be used to, among other things, test how a piece of equipment will respond to one or more shocks during combat. The shock tests conducted with shock generation system 100 can be compliant with, for example, Mil-S-901D Type A, B, C or any other type of shock testing protocols. Shock generation system 100 can be configured to impose simultaneous multi-axis loadings in, for example, the vertical direction, athwartship direction, rotational direction, any other direction(s), or any combination thereof. Some examples of potential uses of shock generation system 100 include: 1) subsidiary component qualification tests for items in qualified principal units having sufficient shock test data for response comparisons (e.g., each component is impact tested after the entire principal unit is explosive tested); 2) principal unit testing to qualify the units for installation on a ship; 3) principal unit testing to screen for poor designs prior to more expensive heavyweight, explosive tests (e.g., as a precursor to more expensive shock tests); 4) as a relatively quick and inexpensive way to test a component during its design and development; 5) engineering studies to examine and compare shock resistance of components and principal units to form a basis for supporting shock test extensions; 6) experiments that examine shock test phenomena (such as, e.g., multi-axis loading effects associated with live mass ratios); and 7) alternative shock qualification testing (e.g., a "belt-and-suspender" approach that compliments other types of shock testing, such as traditional explosive shock tests).

A Deck Simulating Shock Machine ("DSSM"), such as that discussed in the '433 Prov. App, is one embodiment of shock generation system 100. The DSSM improves on and simulates various types of shock tests, including explosive shock tests, which may otherwise use a portion of an actual ship deck or component constructed of the pieces of an actual ship deck to simulate a ship deck's typical modal frequency response. Although shock generation system 100 can be scaled to any size to test any type of component, the proportions shown in FIG. 1 are meant to test, for example, electrical and other shipboard equipment that weigh 425-1250 lbs (~200-575 kg). In addition to simulating a shock from an attack, shock generation system 100 can also impose simultaneous, multi-axis loadings, such as those that simulate a ship's athwartship response to the attack. This is important because a component may be able to withstand certain shocks when standing straight up, but not when rocking back and forth. Shock generation system 100 can also be quickly reset and/or reconfigured (e.g., mass ratio adjusted, elevated to a lesser height) for a second shock test, which simulates the bubble pulse that trails the initial shock wave.

Shock generation system 100 includes cage 102. Cage 102 is shown as being a metal, four-sided rectangular box with a bottom wall, but without any top or side walls. A shock test target (not shown in FIG. 1) can be physically coupled (e.g., welded, bolted, glued, tied, mounted, or any combination thereof) to cage 102. The target can include Class I equipment (i.e., equipment mounted directly onto, e.g., a ship's deck) and/or Class II equipment (i.e., equipment that has its own shock absorbers), and comprise live weight, payload (e.g., dead) weight or a combination thereof. For example, the shock test target can be at least one device, including an electronics module, subsidiary component, principal unit, machinery, weapons system, ammunition, optical device, lighting device, aiming device, system control component, sub-components, and/or anything else that may experience shock during its course of operation (on, e.g., a naval warship). The effective weight of the cage and the target can be, for example, over 6300 lbs. Such an effective weight can still allow for a mass ratio of 5 when using gravity to create the acceleration that causes the initial shock. One skilled in the art will appreciate that different types of shock tests, targets, and shock generation systems can have and/or accommodate different masses and mass ratios.

The target can be coupled to the floor of cage 102, the bars of cage 102, any other part of cage 102, or any combination thereof. Similarly, the target can be rotated in cage 102 for unrestricted orientation during shock tests. Cage 102 can be constructed from any material (such as one or more metals and/or carbon fiber). In embodiments of the present invention that rely on gravity to generate the initial shock (discussed further below), the material(s) used to construct cage 102 can be chosen based on the material(s) having mass sufficient to create the desired impact shock, while still being able to withstand the forces of at least one shock test. In some embodiments, cage 102 can be interchangeable. Interchangeable cages can allow for different cages made from different materials or the ability to test different types of targets. One skilled in the art will appreciate that walls (side, top and/or bottom), which may be barred, partial or full, can also be added to or removed from cage 102. Moreover, additional (payload or live) weight(s) can be added to increase the mass ratio of cage 102 as compared to the target (when, e.g., a heavier target is tested).

At least one swing arm 104 can be coupled to cage 102. FIG. 1 shows four swing arms coupling cage 102 to foundation 106. Swing arm 104 can be made out of any material, such as metal or composite, that can withstand the forces present during a shock test. These forces include rotational, gravitational, and impact forces, among others. Hinging mechanism 108 (or part thereof) may be integrated into either or both ends of each swing arm 104. For example, one end of each swing arm 104 can be coupled to cage 102 by a bolt and clevis that allows the cage to rotate freely in at least one direction during the shock test, or a weld or locking connection that prevents cage 102 from rotating in relation to swing arm 104. The opposite end of swing arms 104 can be coupled to and supported by foundation 106 using hinging mechanisms 108.

Each hinging mechanism 108 can be any device or component that allows the swing arm to move in relation to foundation 106. For example, hinging mechanism 108 can be any type of hinge, such as a ball joint, pivot joint, adjustable clevises, etc, that allows cage 102 to swing during a shock test. Adjustable devises are discussed further below in connection with, e.g., FIG. 4.

Foundation 106 is shown in FIG. 1 as comprising two vertical metal beams, two horizontal metal beams, and two metal support beams. Foundation 106 can also include a cement or other type of base, one or more additional beams (made from any material), rebar and/or any other device or component that helps stabilize shock generation system 100 (none of which are shown in FIG. 1). Foundation 106 can be any type of structure that provides, or at least helps provide, a virtually-fixed support system that only allows for minimal movement, if any, during the operation of shock generation system 100. In some embodiments, foundation 106 has more than about 50 times the mass of any potential target. For example, if shock generation system 100 is designed to shock targets up to of 1250 lbs, foundation 106 should weigh at least 60,000 lbs. As such, shock generation system 100, including foundation 106, can be portable (using a tractor-trailer) or securely fixed to the earth.

Shock generation system 100 can also include one or more locking assemblies, such as locking assembly 110, which are physically coupled to foundation 106. During a shock test, cage 102 may have the tendency to bounce or rebound off of foundation 106 in response to cage 102 being slammed into foundation 106. Locking assembly 110 is designed to minimize such a reaction by coupling cage 102 to foundation 106. The coupling can be done quickly and securely by, for example, catching, latching, locking and/or otherwise minimizing any undesired rebound reaction of cage 102 during a shock test. Locking assembly 110 can be any type or combination of apparatuses, including, e.g., one or more magnetic apparatuses, mechanical apparatuses, any other type of apparatus(es), or any combination thereof. An example of one type of locking assembly is discussed further below in connection with, for example, FIG. 2.

Shock generation system 100 can also include resonation simulator 112, which can simulate an object's typical modal frequency response. Resonation simulator 112 can be used to simulate, for example, an actual ship deck's or other component's frequency response to an initial shock, one or more subsequent shock waves, or combination thereof. Resonation simulator 112 can be an interchangeable component, such as a set of air cylinders or spring tray (which is discussed further in connection with, e.g., FIG. 2). For example, resonation simulator 112 can be tuned to simulate a ship deck that resonates shock waves at 8 Hz. But different ship decks have different resonating frequencies. Accordingly, resonation simulator 112 can be removed from shock generation system 100 and replaced with another resonation simulator (not shown in FIG. 1) that has a different resonating frequency, such as 12 Hz, 16 Hz, 25 Hz, a range of frequencies (such as, e.g., 6-8 Hz or 12-16 Hz), or any other suitable frequency or range of frequencies.

When a spring tray is used as the resonation simulator, it can be modified to resonate at a different frequency without being replaced. Before a shock test, for example, springs can be removed and/or added to resonation simulator 112. The ability to easily interchange and modify resonation simulator 112, allows shock generation system 100 to test and simulate a wide range of components in a relatively short period of time. This is unlike high explosive shock testing, which requires much more time to set up.

Figure 2A:
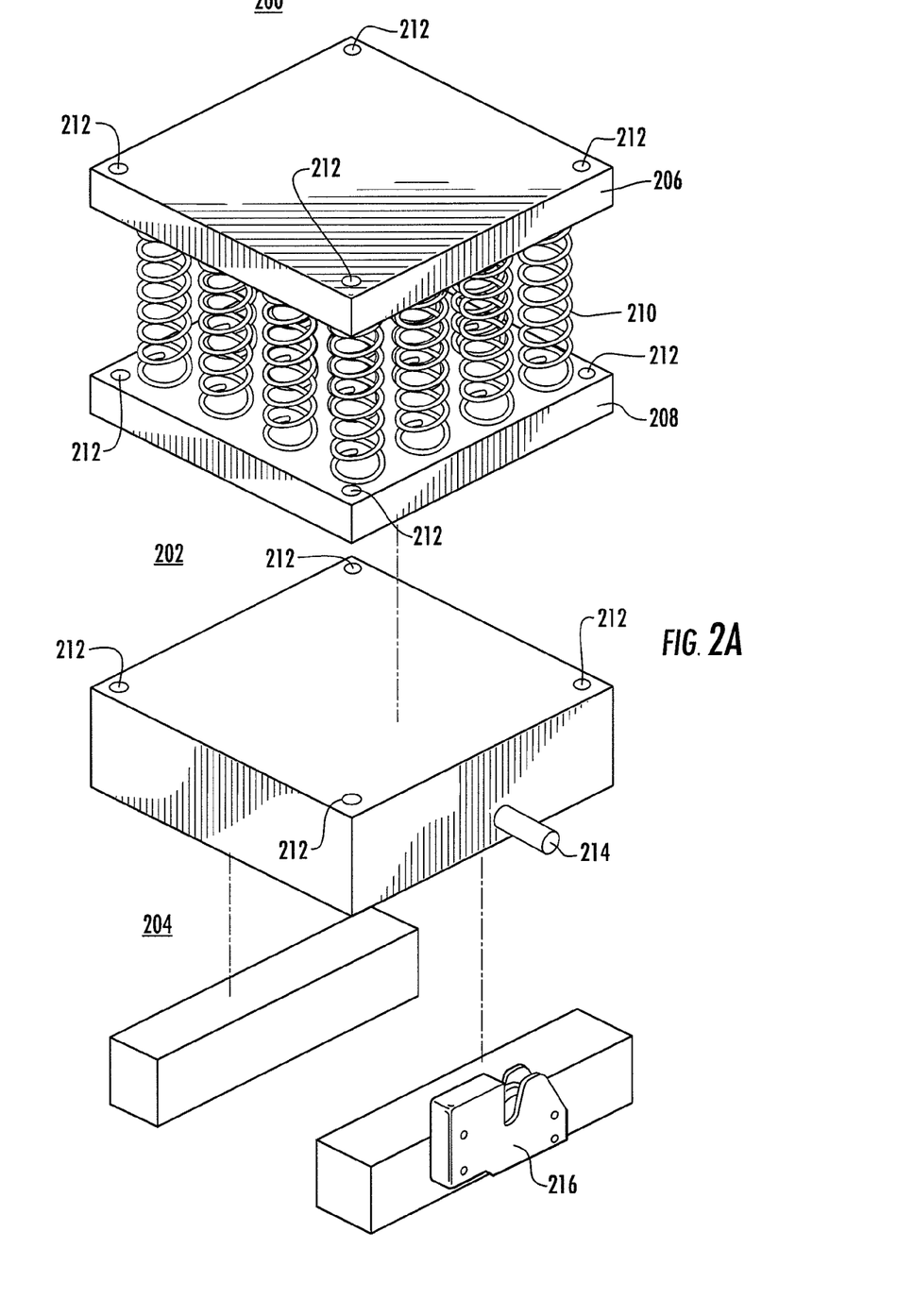
FIGS. 2-4 are exemplary illustrations of components of shock generation systems in accordance with some embodiments of the present invention.

FIG. 2A shows spring tray 200, pin block 202 and impact pad 204, which are three different examples of a resonating component that can be included in resonation simulator 112. Spring tray 200 includes top plate 206, bottom plate 208 and coils 210. Top plate 206 and bottom plate 208 can be made from any suitable material and be any suitable thickness. The suitableness of the material and thickness can be at least partially based on the ability to withstand the forces involved in one or more different types of shock tests. Top plate 206 and bottom plate 208 can also include one or more bolt holes 212 and/or any other means to enable spring coil 200 to be physically coupled to one or more other components (such as cage 102 of FIG. 1).

One or more springs, such as springs 210, can be situated between top plate 206 and bottom plate 208. For example, springs 210 can be physically coupled (e.g., bolted, welded) to top plate 206 and bottom plate 208. Springs 210 can also be tuned to resonate at a specific frequency or at more than one frequency. The number, type and packaging of springs included in springs 210 can also vary. For example, each spring can be coated with a dampening material (such as a plastic or rubber) and/or individually packaged between top plate 206 and bottom plate 208. In some embodiments, springs 210 can also consist of a single, relatively large spring, rather than a series of springs. In other embodiments, each of springs 210 are the same and, in yet other embodiments, there is a mixture of different springs or other components (such as double acting high pressure air cylinders) included in springs 210.

Pin block 202 can be mounted to the bottom of spring tray 200. For example, bolts can be inserted into bolt holes 212 and a washer can be used to physically couple pin block 202 to spring tray 200. Pin block 202 also includes locking pin 214. Locking pin 214 can be received by latch assembly 216, which is coupled to pad 204. Latch assembly 216 can comprised a fork that rotates and catches locking pin 214 (similar to how a car door's locking mechanism functions). In some embodiments, multiple locking pins and latch assemblies can be integrated into pin block 202 and pad 204.

Pad 204 can be part of or coupled to the shock generation system's foundation. One skilled in the art would appreciate that locking pin 214 could be integrated into the cage, spring tray 200, or other moving component of the shock generation machine, so long as latch assembly 216 is securely coupled to the foundation and is configured to receive the locking pin(s). For example, pin block 202 could be omitted from the shock generation system if the pin(s) are integrated into spring tray 200 (which is similar to the embodiment discussed below in connection with FIG. 2C). One skilled in the art would also appreciate that a number of locking assemblies can be used simultaneously and may be required for shock tests of relatively heavier targets.

Figure 2B:
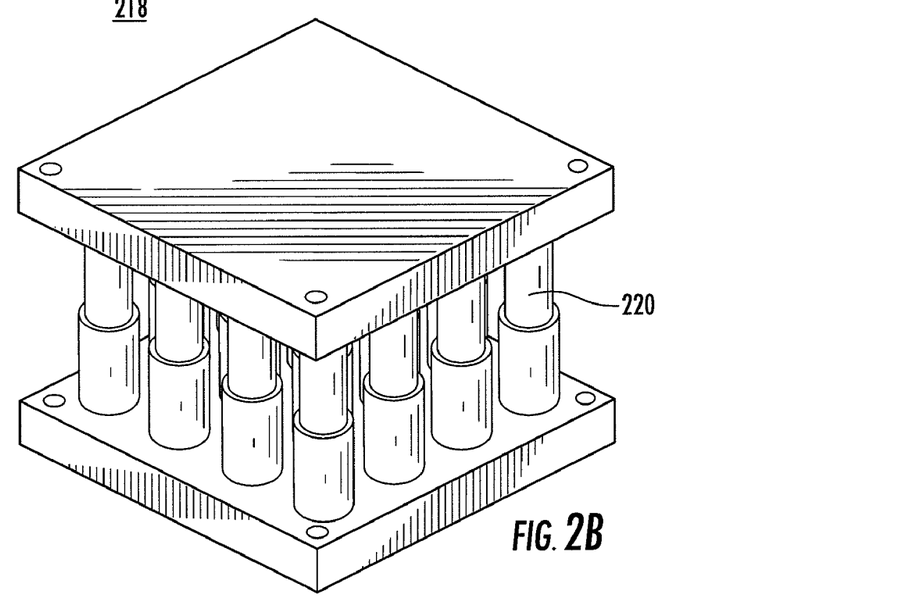

FIG. 2B shows resonation simulator 218, which is alternative design of a frequency resonation simulator. Instead of springs, resonation simulator 218 includes air cylinders 220, which can be coupled to a cage (and pin block), such as those discussed above. Similar to the other resonation simulators discussed above, resonation simulator 218 can be used during a shock test to simulate the modal frequency response of an object (such as, e.g., a ship's deck). The pressure in each air cylinder 220 can be individually controlled, which can affect the frequency response of air cylinders 220 during a shock test. One skilled in the art would appreciate that a hybrid of resonation simulator 218 and spring tray 200, which includes both springs and air cylinders, could also be used to simulate the modal frequency response of an object.

Figure 2C:
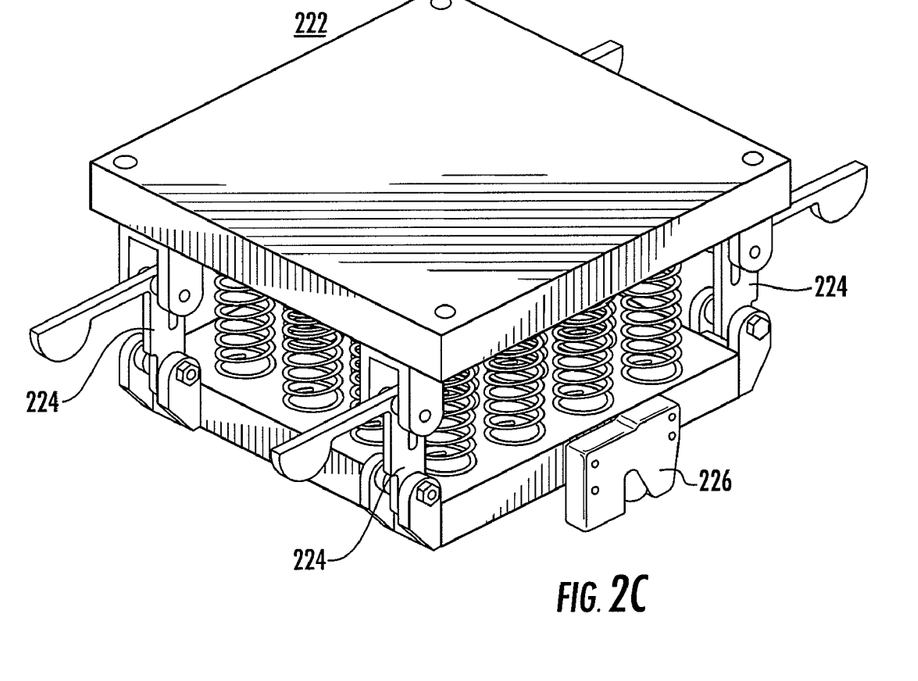

FIG. 2C shows spring tray 222, which includes latches 224. Spring tray 222 can function the same as or similar to resonation simulator 218 and/or spring tray 200 discussed above. Latches 224 are examples of quick release latches that can allow the springs of spring tray 222 to be locked in a compressed, or partially compressed, state until the impact with the foundation occurs. Latches 222 can be used to create larger shocks at the modal frequencies being simulated. For example, quickly releasing the potential energy of the springs of spring tray 222, increases the modal response associated with coupled target in cage system. In addition, it imparts higher frequency input to the system as a result of the shorter rise time of the initial shock, resulting from the pre-compression of the springs. Accordingly, one or more of the multi-axis forces, such as the force associated with vertical impact velocity, can also be influenced by the shorter rise time. Although four latches 222 are shown in FIG. 2C, one skilled in the art will appreciate that more or less latches can be used in accordance with some embodiments of the present invention.

One or more hydraulic cylinders (not shown) or any other compression mechanism (which can be automated, manual or a combination thereof) can provide the force necessary to compress the springs of spring tray 222 and/or lock latches 224. The compression mechanisms can be structurally integrated into the shock generation system or be removable. Removable compression mechanisms can compress the springs before the shock test and then be removed prior to elevating and/or dropping the cage. In response to the impact with the foundation, latches 224 are unlocked and the potential energy stored in the compressed springs of spring tray 222 is released. An example of a locking mechanism that can be used with each of latches 224 is discussed below in connection with, e.g. FIGS. 3A-D.

In addition, spring tray 222 includes slam lock mechanism 226, instead of a locking pin. The other part(s) of the locking assembly (e.g., the locking pin) can be integrated into the foundation of the shock generation system (see, e.g., FIG. 1). Additional slam locks or other locking devices could also be integrated into spring tray 222 (none of which are shown).

Figure 3A:
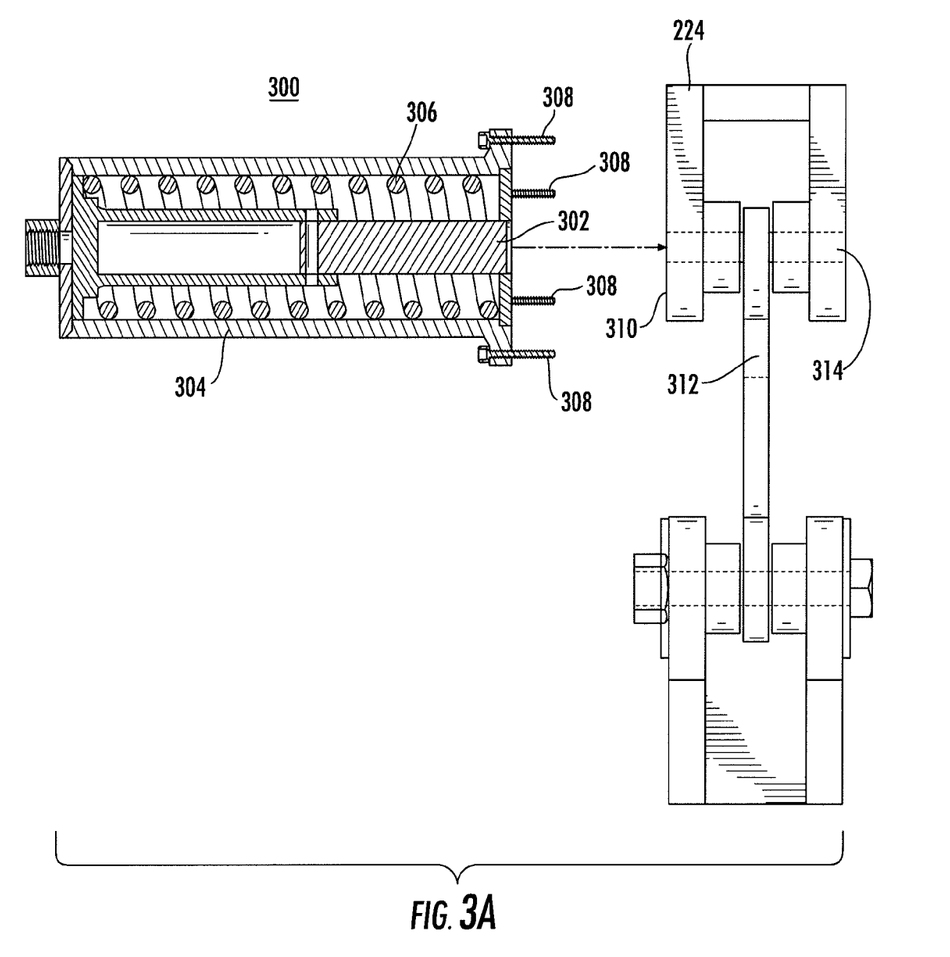
Figure 3B:
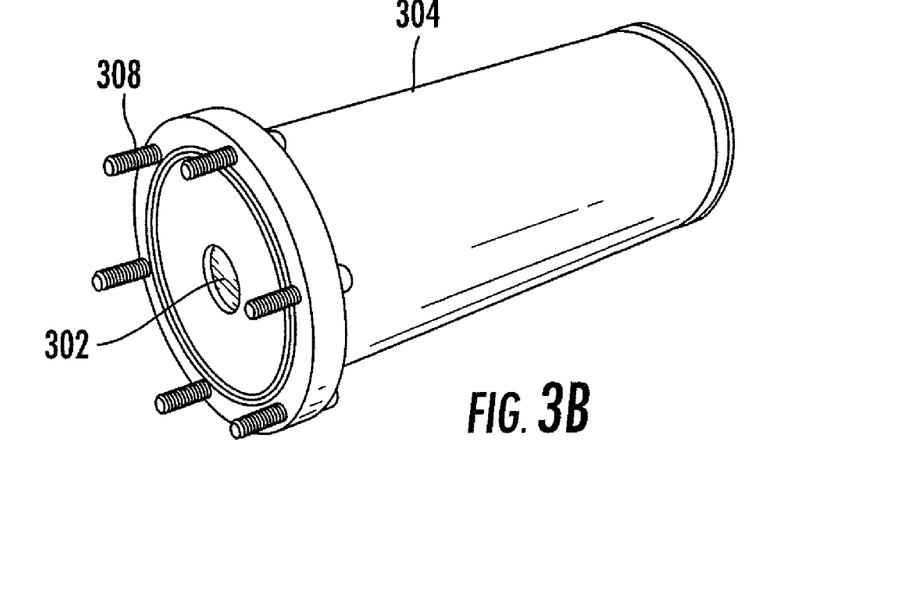
Figure 3C:
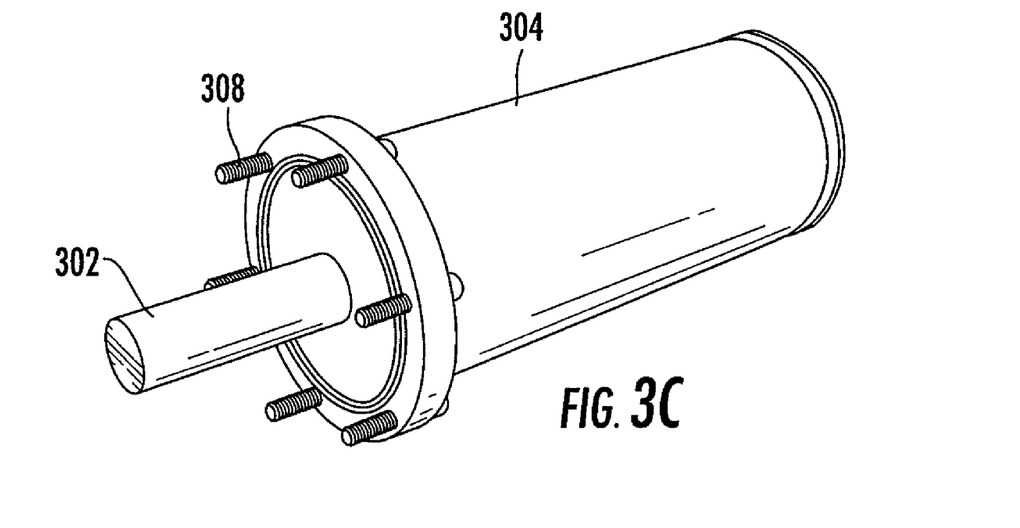

FIGS. 3A-3C show impact release mechanism 300, which is one example of an apparatus that can keep each latch 224 locked (thereby keeping the spring coils compressed) until impact. FIG. 3A is a cut-away view and FIGS. 3B and 3C are not.

Impact release mechanism includes pin 302, inside of enclosure 304 and physically coupled to spring 306. FIGS. 3A and 3B show impact release mechanism 300 with pin 302 retracted. Before a shock test and while the resonation simulator component (such as those discussed above) is being compressed, the application of pressure can cause pin 302 to be extended out of enclosure 304. FIG. 3C shows pin 302 as extended outside enclosure 304.

Pin 302 can also be extended into latch 224, when the resonation simulator is being compressed and screws 308 (or any other means) are used to mount impact release mechanism 300 onto latch 224. Latch 224 can include leading hole 310, elongated hole 312 and posterior hole 314. Elongated hole 312 can allow for unconstrained cage displacement in the downward direction during set up and after impact.

The pressure used to compress the resonation simulator can be removed after pin 302 is extended through leading hole 310, elongated hole 312 and posterior hole 314. The removal of the compression pressure will cause the springs of the resonation simulator to expand and friction will lock pin 302 in latch 224 (i.e., prevent spring 306 from retracting pin 302 into enclosure 304). The amount of friction exerted should exceed the amount of force created by spring 306 while compressed.

When an impact occurs during a shock test, the resonation simulator is compressed further, which causes the frictional loading to be removed from pin 302 as it slides down elongated hole 312 in the linking portion of latch 224. The potential energy stored in compressed spring 306 is released and, in response, pin 302 is retracted back into enclosure 304. Without pin 302 extending through latch 224, the resonation simulator is free to fully expand and oscillate freely. The initial full expansion of the resonation simulator will increase the impact velocity or velocities (which are discussed further below) experienced by the target.

Figures 4A, 4B:
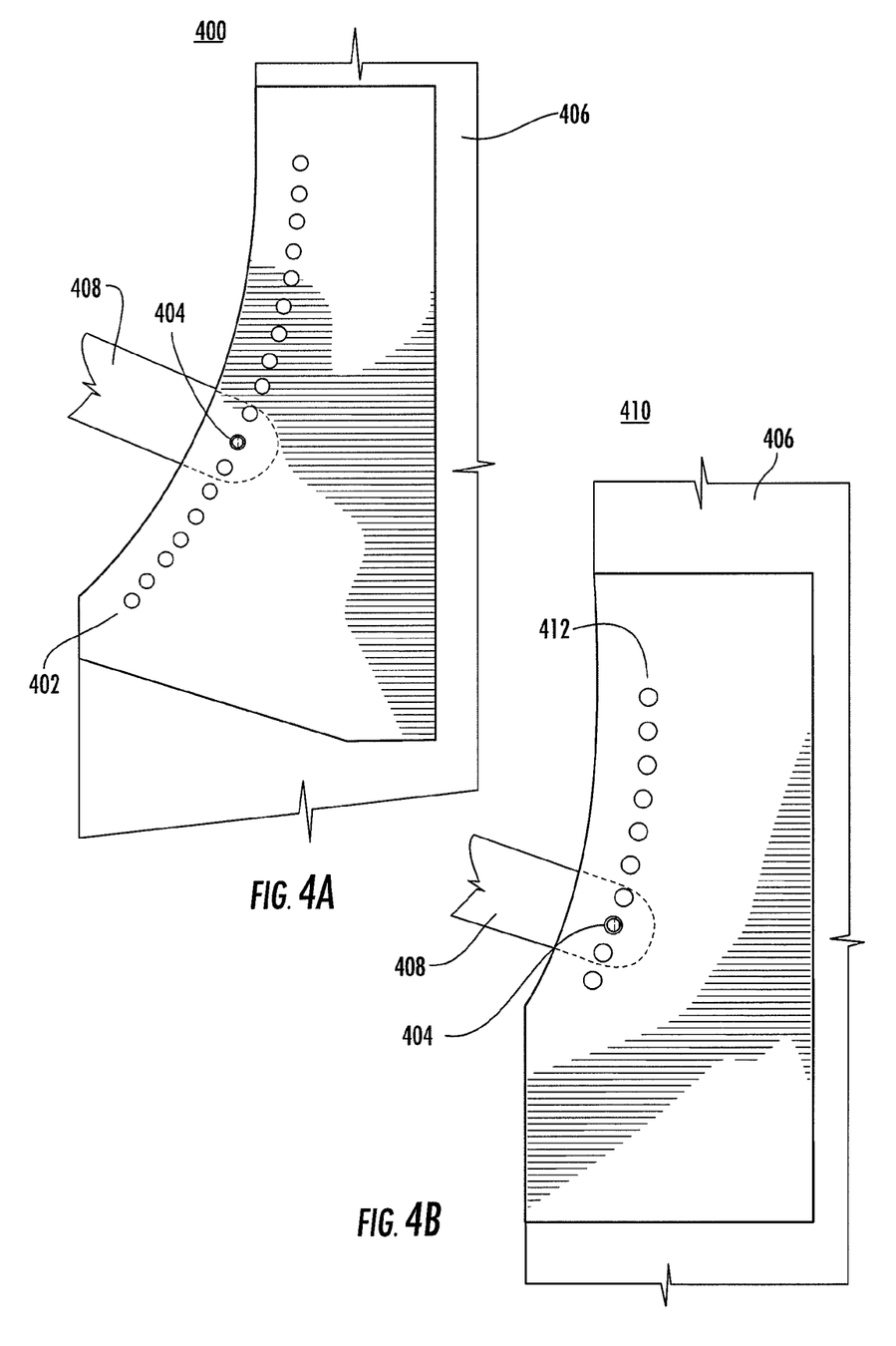

FIG. 4A shows hinging mechanism 400, which uses adjustable clevis 402 and clevis pin 404 to physically couple foundation 406 to swing arm 408. Foundation 406 and swing arm 408 function substantially similar to or the same as foundation 106 and swing arms 104, respectively of FIG. 1.

Adjustable clevis 402 includes a series of holes, which are each separated at predetermined intervals. For example, each hole can be offset by 2 degrees from the previous hole. In such embodiments, swing arm 408 also has a hole and clevis pin 404 is inserted through both the hole of clevis 402 and the hole of swing arm 408. Each of the holes of clevis 402 can cause the target to experience different forces during a shock test. Different shock test configurations, including the effect of various clevis angles, are discussed further below in connection with, e.g., FIGS. 5A and 5B.

Although hinging mechanism 400 may serve as both the top and bottom hinging mechanisms, some embodiments of the present invention can utilize different hinging mechanisms for the top swing arms than the bottom swing arms. For example, hinging mechanism 400 may be used for top swing arms and hinging mechanism 410 can be used for bottom swing arms. Hinging mechanism 410 also includes clevis pin 404 and is used to couple foundation 406 to swing arm 408. Adjustable clevis 412 is one unique feature of hinging mechanism 410 as compared to hinging mechanism 400. In particular, the intervals separating the holes of adjustable clevis 412 can be spaced differently (e.g., 1 degree from each other) than the clevis holes of adjustable clevis 402. The difference in spacing of clevis holes of adjustable clevis 412 versus the holes of adjustable clevis 402, can enable, among other things, a number of unique, medium weight shock tests to be conducted, some of which are discussed further below in connection with, e.g., FIGS. 5A and 5B.

One skilled in the art will appreciate that any type or combination of hinging mechanisms can be used in any manner without departing from the spirit of the present invention. For example, a gravity shock generation system (which is discussed further below) could be engineered to utilize hinging mechanism 400 for one or more lower swing arms and hinging mechanism 410 for one or more upper swing arms. One skilled in the art will also appreciate that more or less swing arms can be used and that any type of hinging mechanism can be used to support and couple the swing arm(s) to the foundation.

Figure 5A:
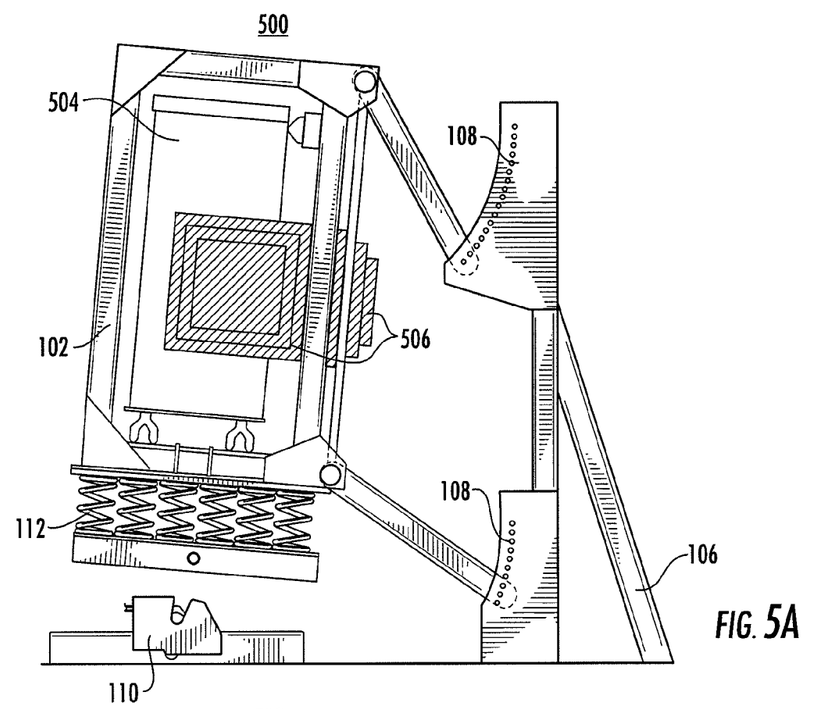
FIGS. 5A-5B are exemplary illustrations of a gravity shock generation system in an positive potential energy position and a zero potential energy position in accordance with some embodiments of the present invention.
Figure 5B:
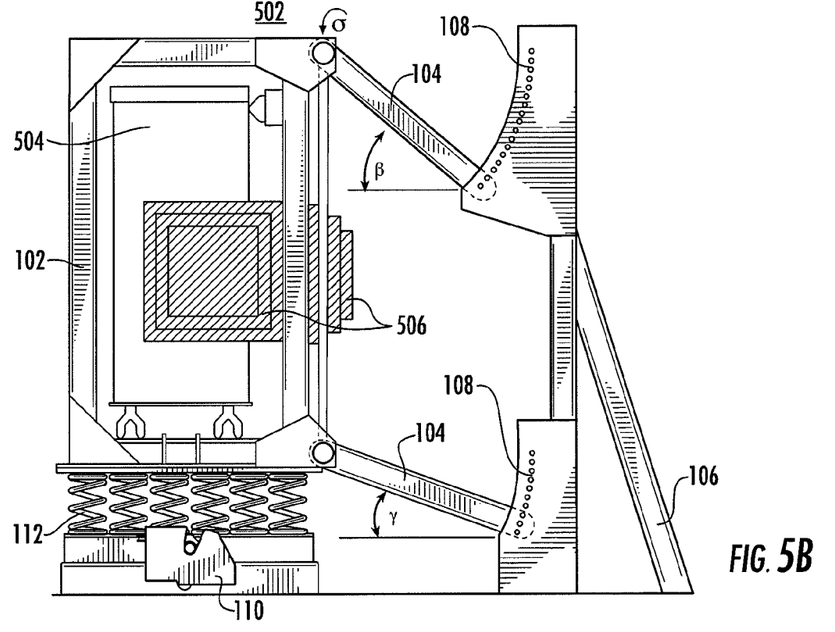

FIGS. 5A and 5B show one example of how a physical impact shock test can be conducted in accordance with embodiments of the present invention. Shock generation systems 500 and 502 are substantially the same as shock generation system 100 of FIG. 1. Accordingly, reference numbers from FIG. 1 are used in FIGS. 5B and 5B to refer to like components. In addition to the components and devices discussed in connection with FIG. 1, FIGS. 4B and 5B include target 504 and weights 506. Although target 504 is shown as a cabinet housing Class II equipment, target 504 can be any type of shock target device, such as those discussed above. Weights 506 can be any type of dynamic or dead weight(s) that are mounted to cage 102 and/or target 104, and are used to increase the mass ratio (also discussed above). For example, weights 506 can be constructed from steel or any other material, and can be solid, hollow, or (partially) filled with a fluid. One or more of weights 506 can removable or part of cage 102.

Shock generation system 500 is an example of a gravity shock generation system in the elevated position. As used herein, a gravity shock generation system uses potential energy based on the Earth's gravitational force (about 9.8 meters per second squared) to create the initial impact shock. Explosives can therefore be omitted from the shock tests, which makes the shock tests inherently safer and increases the number of locations at which shock tests can be conducted. The desired initial impact shock is based on the impact velocity based on the equation: $h=V^2/(2\,g)$, where "g" is the Earth's gravitational force, "V" is the impact velocity and "h" is the elevated height. In other embodiments, such as those that use pistons or other mechanical apparatuses instead or in addition to the force of gravity, g can equal the cumulative force being applied to cage 102.

The target can be elevated to the height in any number of ways. For example, a winch, crane or fork lift (none of which are shown) can lift cage 102. Shock generation system 500 can also comprise one or more motors and circuitry that cause swing arms 104 to elevate cage 102. After cage 102 is elevated to the height, it can be allowed to fall and slam into foundation 106. Upon impact, locking assembly 110 physically couples cage 102 to foundation 104, thereby minimizing any undesired rebounding action that may otherwise take place. FIG. 5B shows shock generation system 502, which is shock generation system 500 in the down position (i.e., after the potential energy has been released). The initial impact and/or any force generated from the initial impact can be measured by one or more sensors (not shown). For example, one or more accelerometers or other shock sensors can be affixed to various parts of shock generation system 500. The data collected by the sensors can be uploaded to a computer (not shown) and used for diagnostic or other purposes. Similarly, data from target 504 can also be uploaded to a computer (not shown) and used for diagnostic or other purposes.

FIG. 5B also shows how the impact angle can be adjusted using hinging mechanisms 108. Hinging mechanisms 108 are shown in FIG. 5B as being two different types of adjustable devises. Velocities in the Y, Z and θ directions, which are created during a shock test, can be preconfigured by positioning swing arms 104 at specific angles relative to the plane of foundation 106. The angles are represented by "β" and "γ" in FIG. 5B.

β represents the angle between a hypothetical line parallel to the ground and a line running through the upper swing arm(s). β can effect the rotational velocity, θ, imparted onto target 504 during impact, as well as vertical velocity in the Z (i.e., downward) direction. In a gravity shock generation system, the vertical velocity is proportional to the height, h, and β can cause different portions of target 504 to fall from different heights. The rotational velocity at impact is correlated to the difference between β and γ. Explosive shock tests generally have a maximum angular velocity of 0.55-0.95 radians per second, which can also be created using shock generation system 502.

γ represents the angle between a hypothetical line parallel to the ground and a line running through the lower swing arm(s). γ is related to the swing arm impact angle and can be calculated based on the desired vertical to athwartship ("VA") ratio. In particular, $\gamma=a\sin(1/\sqrt{1+VA^2})$. The VA ratio represents the amount of athwartship motion as compared to the vertical (or downward) velocity during impact. For comparison, the VA ratio of heavyweight explosive shock tests range from ~2 to 3, which would translate to a γ of ~26.565° to 18.435°.

As such, one or more adjustable devises allow shock generation system 502 to be configured to impact foundation 106 at a particular angle, which allows for simultaneous simulation of a number of forces when the moving masses (e.g., cage 102, target 504, dead weights 506, etc.) are taken into consideration. In other words, the magnitude and direction of the initial shock, athwartship forces and rotational forces can be controlled by the angles β and γ. This allows a shock testing machine, in accordance with embodiments of the present invention, to simulate, for example, a surface ship's impact and athwartship response to an enemy attack. The quality of the shock test is enhanced by the ability to tune resonation simulator 112 to simulate any object's modal frequency response to the initial shock. Because target 504 can be orientated in any manner within cage 102 (as discussed above), a number of different, but accurate, shock tests can be conducted relatively quickly and inexpensively.

One skilled in the art will appreciate that the shock generation systems of embodiments of the present invention are not limited to using gravity and that the arms can be motorized. Motorized arms can enable the shock generation system to be mounted to a wall (instead of the ground) and test objects that may be mounted to, e.g., the walls or hulls of ships. For example a shock generation system can be mounted to a wall or other vertical foundation structure, so that the "bottom" of the shock generation system is perpendicular to the ground. This would allow the force of gravity to act in the downward direction, while the forces created during the shock test act in a sideways direction.

The controls and calculations used to determine the h, β, γ and any other variable, can be automated. Embodiments of the present invention can utilize a 6 degree of freedom simulation software tool called SIMPLE (which is an acronym for Shock Isolation Mount Predictions and Loading Estimates). SIMPLE can be used to calculate the forces resulting from different types of shock generation systems. For example, the dimensions of a shock generation system and target can be inputted into SIMPLE as well as the desired impact responses of the shock generation system (e.g., initial shock force, rotational force, athwartship force, resonating frequencies, etc.). SIMPLE can then be programmed to model the required positions and velocities of the shock generation system with, e.g., equations of motion (such as those discussed above) that describe the accelerations and subsequent coupling of the shock testing machine with the foundation. SIMPLE can also be programmed to consider the effect of additional components that may be used in a shock test, such as an Under Unit Test component which is commonly used in explosive shock tests. SIMPLE's or any other control software's outputs can be translated into settings and/or automated controls for real shock tests. If, for example, a shock generation system in accordance with embodiments of the present invention were outfitted with the appropriate motors and circuitry, SIMPLE can be calibrated to simulate a particular shock generation system's design, and then send outputs to the shock generation system that include settings and/or commands associated with drop height, swing arm angles at impact (e.g., β and γ), frequency of a resonation simulator (even, e.g., the number and/or types of springs to be used), and any other variable that may effect an impact shock test.

FIGS. 6A-6D show process 600, which outlines exemplary steps of a method that can be implemented by a computer and/or user(s) to execute a shock test in accordance with some embodiments of the present invention. Process 600 starts at step 602 and proceeds to step 604.

Figure 6A:
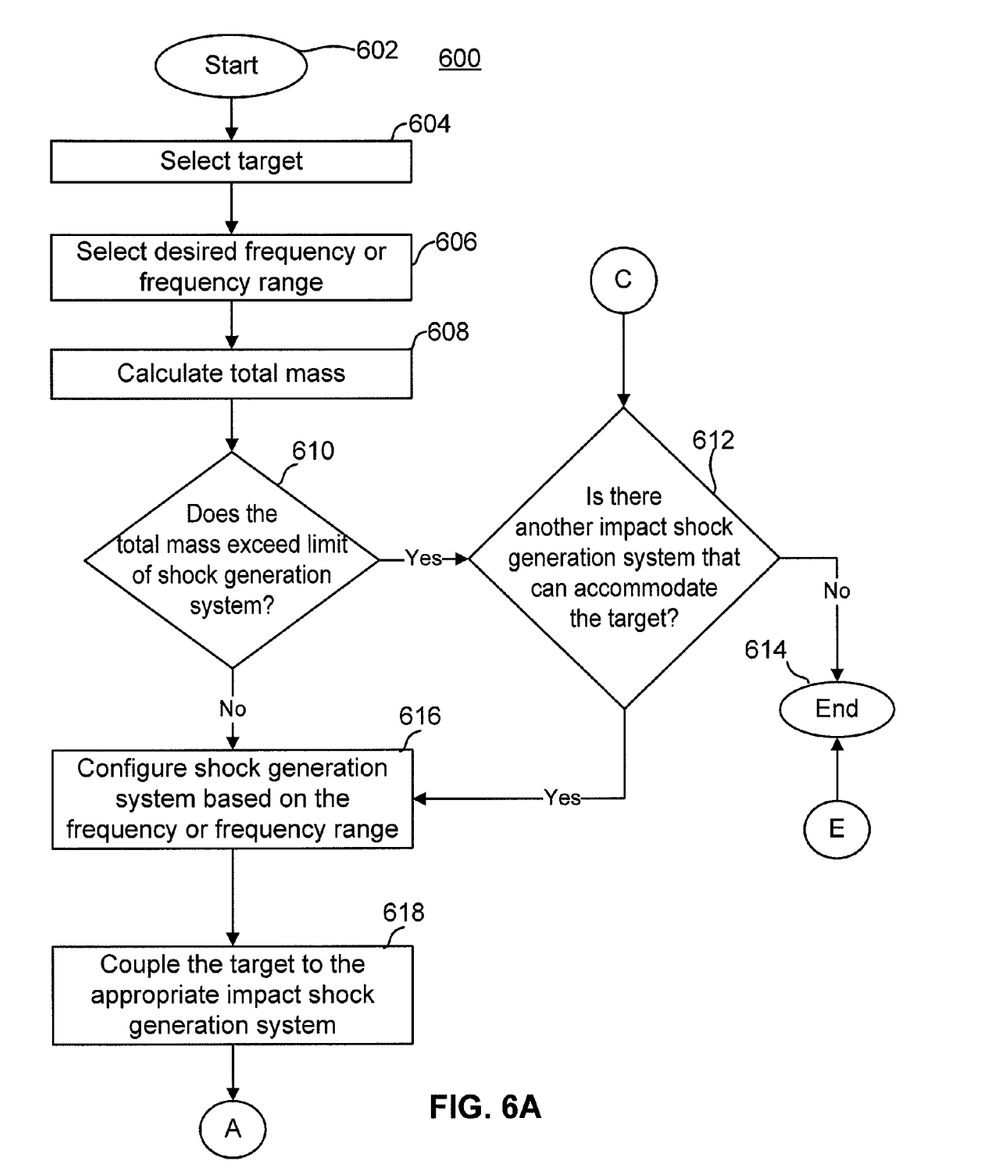
FIGS. 6A-6D is an exemplary flow chart that shows the steps of a method that can be preformed in accordance with some embodiments of the present invention.

At step 604, a target is selected. The target can be any device, apparatus, portion thereof, or anything else to be shock tested. Some additional examples of targets are discussed above in connection with, e.g., FIG. 1.

Next is step 606, at which the desired frequency or frequency range is selected. As discussed above, a particular object, such as a ship's deck for example, can have a specific modal frequency response.

Next the total mass is calculated at step 608. The total mass can include the mass of the cage, the target, and any other component of the shock generation system that can influence the shock test. This can be completed in any number of ways, including using a scale or other mass calculating sensor(s). The target's and/or total mass can be used later in process 500 to execute a number of calculations and make determinations.

One such determination occurs at step 610, during which it is determined whether the total mass and dimensions exceed the limit of the intended shock generation system. Different shock generation systems can be comprised of different components and be designed to accommodate different size targets. For example, a shock test system with a 50,000 lb foundation may only be able to accommodate a 1,000 lb target. As another example, a cage of a shock generation system may restrict the shape or other dimensions of a target. In response to determining that the total weight exceeds the recommended limit of the shock generation system, process 600 proceeds to step 612.

At step 612, a determination is made as to whether or not there is another impact shock generation system available that can accommodate the weight and dimension requirements associated with the target. If not, an explosive floating shock platform test can be recommended and process 600 can end at step 614.

However, process 600 proceeds to step 616 in response to determining at step 610 that there is another impact shock generation system available, which can accommodate the target's mass (and dimensions). Process 600 will also proceed to step 616 in response to determining at step 610 that the target's mass and dimensions do not exceed the limit of the first intended shock generation system.

At step 616, the shock generation system is configured based on the frequency range or range of frequencies. Configuring the shock generation system can include selecting a resonation simulator, adjusting a resonation simulator (e.g., adding or removing springs/air cylinders), any combination thereof, or making any other adjustments that can influence the frequency at which the target will resonate in response to the impact shock.

Next is step 618, at which the target is coupled to the appropriate impact shock generation system. The target can be, for example, bolted, welded, mounted or otherwise attached to a cage, platform, or any other type of component designed to receive the target. In addition, the target can be coupled to the shock generation system in any suitable orientation (e.g., up-side down, right-side up, etc.). Subsequent shock tests can be executed with the orientation of the target being the only variable that changes.

Figure 6B:
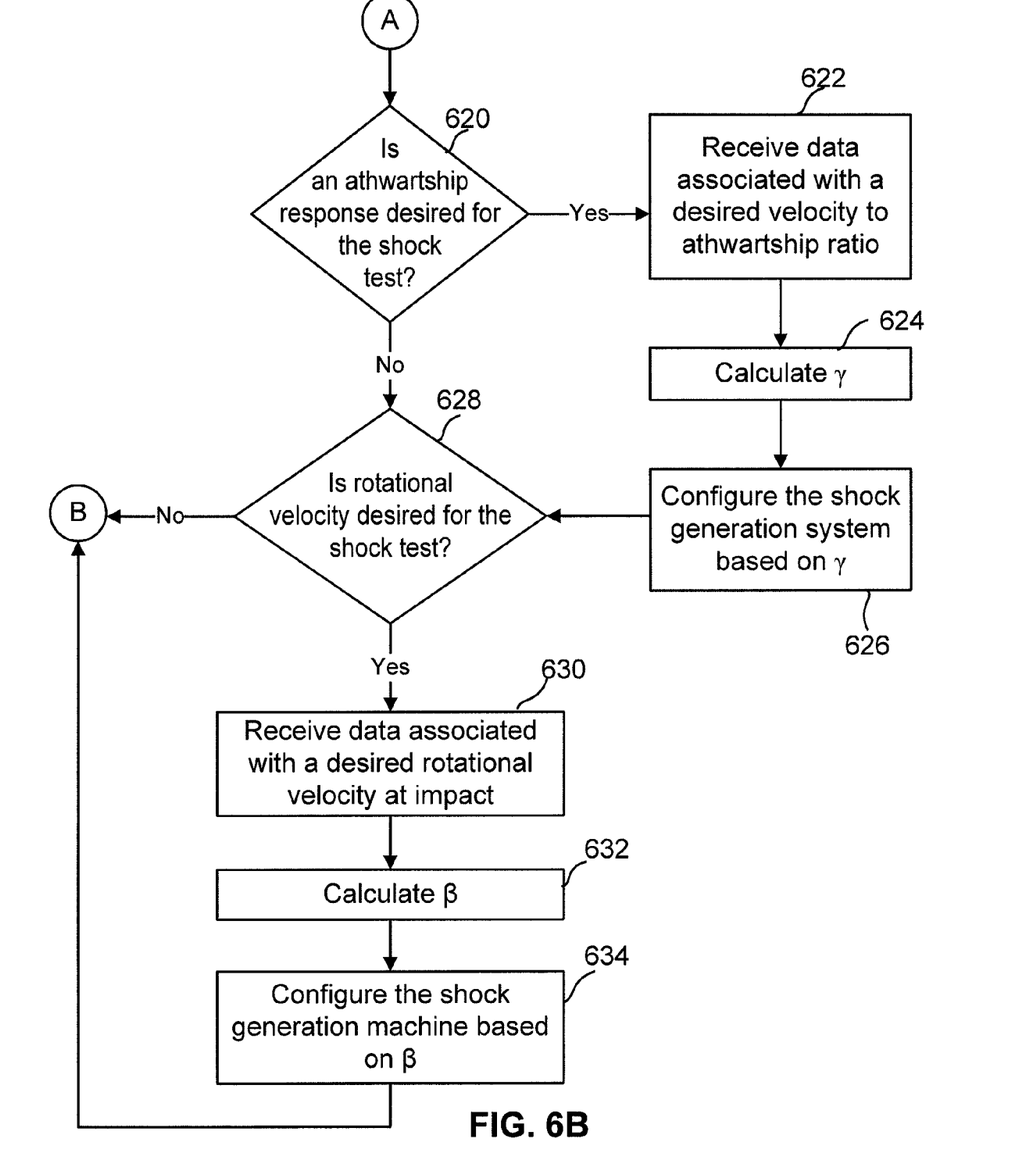

Next is step 620 shown in FIG. 6B, at which a determination is made as to whether or not an athwartship response is desired for the shock test. In response to determining that an athwartship response is desired, process 600 proceeds to step 622.

At step 622, athwartship setting data is received (from a user, computer, remote server, etc.). The athwartship setting data is associated with a desired VA ratio (discussed above). At step 624 the VA ratio can be used to calculate γ and at step 626 the shock testing machine is configured based on γ. Configuring the shock testing machine can comprise, for example, adjusting one or more hinging mechanisms that couple one or more swing arms to the foundation (by placing one or more clevis pins into the corresponding clevis hole(s)). As another example, an automated, motorized system may automatically adjust the swing arm's physical position to correspond with γ.

Process 600 then proceeds to step 628. Step 628 also follows step 620 in response to there being no athwartship response desired for the shock test. At step 628, a determination is made as to whether a rotational velocity is desired for the shock test. When a rotational acceleration is desired, process 600 proceeds to step 630.

At step 630, rotational setting data is retrieved (from a user, computer, remote server, etc.). The rotational setting data is associated with a desired rotational velocity to occur at impact (discussed above). At step 632 the desired rotational velocity can be used to calculate β, and at step 634 the shock testing machine is configured based on β. Configuring the shock testing machine can comprise, for example, adjusting one or more hinging mechanisms that couple one or more swing arms to the foundation (by placing one or more clevis pins into the corresponding clevis hole(s) or by any other means). As another example, an automated system can be used to adjust the swing arm's physical position to correspond with β.

Figure 6C:
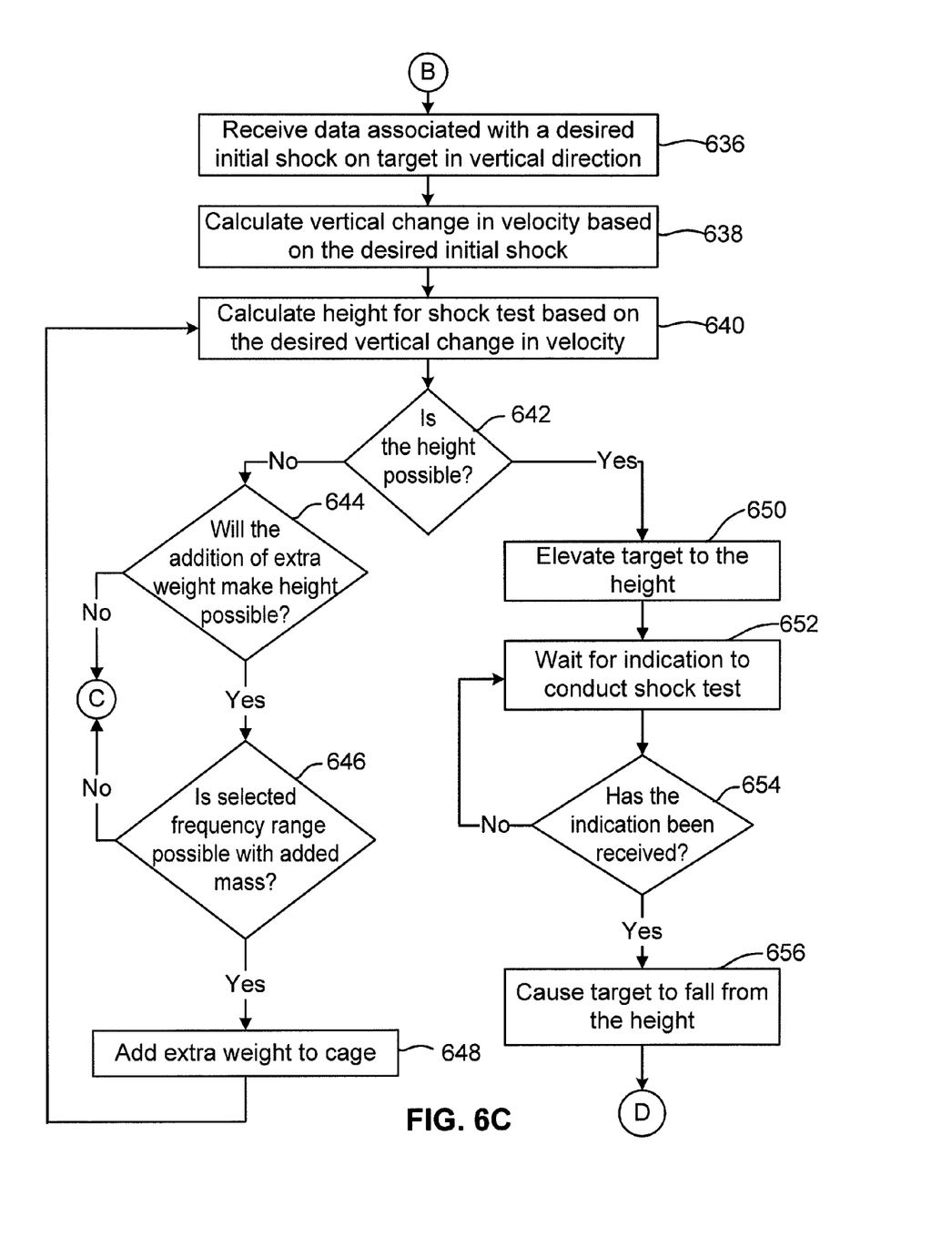

After step 634 or after determining at step 628 that a rotational velocity response is not desired, process 600 proceeds to step 636 of FIG. 6C. At step 636, vertical setting data is received that is associated with the desired initial shock in the vertical direction. The vertical setting data is used at step 638 to calculate a vertical change in velocity, and at step 640 the height for the shock test is calculated based on the desired change in vertical velocity at impact. In the gravity shock test, the height is a function of gravity and the total mass of the target and other components (e.g., cage) that are falling.

After the height required to create the necessary change in velocities is determined, a determination is made at step 642 as to whether or not the shock generation system can accommodate the requirements. In determining whether the height is possible, the process may include analyzing the impact of using/adding a latching system that allows the resonation simulator to be compressed and released upon impact (as discussed above in connection with, e.g., FIGS. 3A-3C). In some embodiments of the present invention, the shock generation system can include one or motors that can create or assist gravity in creating the vertical impact force, which will also be taken into consideration at step 642. In response to determining at step 642 that the shock generation system is physically unable to accommodate the test requirements, a determination is made at step 644 as to whether or not the addition of extra weight would increase the total mass enough to have the required velocity, etc. If not, process 600 returns to step 612 of FIG. 6A, which is discussed above.

In response to determining that extra weight will enable the shock generation system to conduct the shock test accordingly, extra weight is added to, for example, the cage. The total mass can then be recalculated, if necessary, to include the mass of the extra weight. One skilled in the art would appreciate that extra weight need not be added in all embodiments of the present invention and, in some embodiments, it may be disadvantageous to mount the weight directly onto the target as it may create false results (instead of the shock generation machine).

Returning to step 642, in response to determining that the shock generation system should be physically able to fulfill the test requirements, process 600 proceeds to step 650. At step 650, the target (and the cage, extra weights, etc.) are elevated to the height. The elevation can include the use of any type of lifting mechanism or device, including a winch, crane, fork lift, or any other means. In some embodiments, the locking assembly may have to be released before the evaluation takes place. For example, the locking pin may have to be removed from the latch, or power to a magnetic locking system may have to switched OFF.

At step 652, the target remains suspended above the foundation until an indication is received that triggers the fall. The indication can be electrical signal, the removal of a pin from a quick release mechanism, a vocal command, or anything else that causes the target, cage, etc. to fall from the height and slam into the foundation. At step 654 a determination is made as to whether an indication has been received. If not, step 652 is repeated.

Once a determination is made at step 654 that the indication has been received, process 600 advances to step 656.

At step 656, the target falls from the height after, e.g., the quick release mechanism is activated, if necessary. The fall can be caused by gravity, one or more motors, a combination thereof, and/or any other means. The target can also fall at an angle, based on β and/or γ, if applicable, which can cause the target to experience a rotational and/or athwartship velocity response upon impact. The impact can impart a force through the springs and into the cage, which affects the target.

Figure 6D:
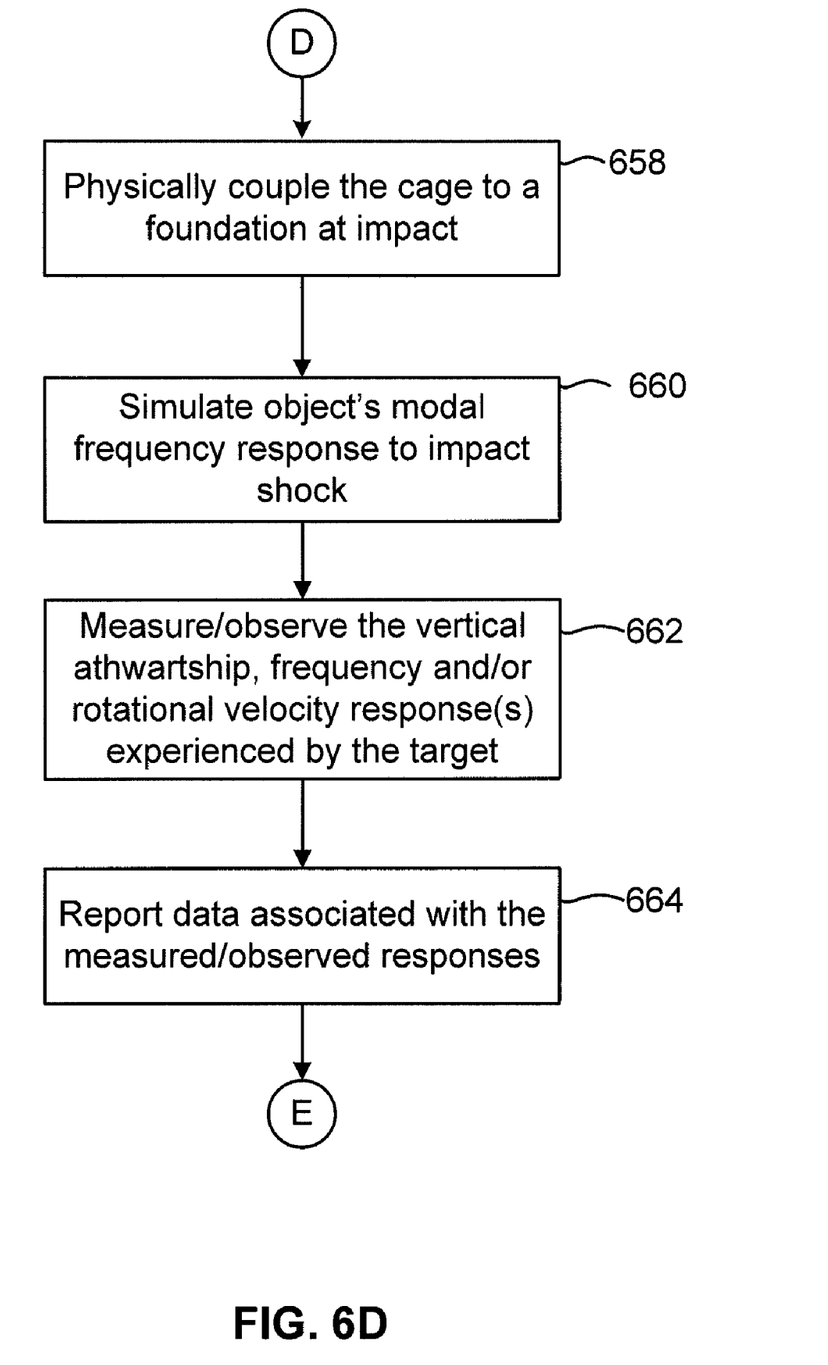

At step 658 of FIG. 6D, the target is physically coupled to the foundation of the shock generation system. Physically coupling the target to the foundation may include, for example, using a locking system that quickly couples the resonation simulator to the foundation, wherein the resonation simulator is bolted to the cage, on which the target is mounted. The target is also shocked as a result of the impact and, if the resonation simulator was compressed, the energy from the resonation simulator can be released in response to the impact.

At step 660, an object's modal frequency response is simulated by, e.g., a resonation simulator. Examples of objects and means for simulating an object's modal frequency are discussed above.

To confirm that the vertical, athwartship, frequency and/or velocity responses are accurate, each can be measured and/or observed at step 662. For example, one or more accelerometers, cameras, and/or any other sensor can be used to measure and/or observe the impact, the target's reaction, shock generation machine's reaction, etc.

The data compiled from the sensors and measured during the preceding steps can be reported at step 664 to, for example, a computer, remote server, display device, combination there of, or any other device(s). Process 600 then proceeds to step 612 of FIG. 6A and ends.

Many modifications and other embodiments of the inventions set forth herein will come to mind to one skilled in the art to which these inventions pertain having the benefit of the teachings presented in the foregoing descriptions and the associated drawings. For example, various steps and/or components could be added to, omitted from and/or combined within process 600 and/or any of the embodiments discussed above. Therefore, it is to be understood that the inventions are That which is claimed:

1. A shock generation system, comprising:
   a cage configured to receive a target device that is to be shock tested;
   at least one swing arm connected to the cage;
   a resonation simulator that simulates a frequency response resulting from to a shock; and
   a locking assembly that is used to secure the cage in response to the shock.

2. The shock generation system of claim 1 further comprising:
   at least one hinging mechanism; and
   a foundation structure, wherein:
      the at least one hinging mechanism connects the at least one swing arm to the foundation structure.

3. The shock generation system of claim 2, wherein the locking assembly comprises:
   a locking pin; and
   a latch assembly that is integrated into the foundation structure.

4. The shock generation system of claim 2, wherein the locking assembly comprises:
   a locking pin; and
   a latch assembly that is integrated into the resonation simulator.

5. The shock generation system of claim 2, wherein the locking assembly comprises:
   a locking pin; and
   a latch assembly that is integrated into the cage.

6. The shock generation system of claim 2, wherein the locking assembly comprises:
   a latch assembly; and
   a locking pin that is integrated into the foundation structure.

7. The shock generation system of claim 2, wherein the locking assembly comprises:
   a latch assembly; and
   a locking pin that is integrated into the resonation simulator.

8. The shock generation system of claim 2, wherein the locking assembly comprises:
   a latch assembly; and
   a locking pin that is integrated into the cage.

9. The shock generation system of claim 2, wherein the resonation simulator is configured to simulate how a ship deck resonates in response to a close proximity explosion.

10. The shock generation system of claim 2, wherein the resonation simulator comprises:
    at least one tunable coil mount;
    a top plate; and
    a bottom plate, wherein the at least one tunable coil mount is located between the top plate and the bottom plate.

11. The resonation simulator of claim 10, further comprising:
    at least one impact release latch mechanism.

12. The shock generation system of claim 2, wherein the resonation simulator is configured to resonate at 6 Hz to 8 Hz.

13. The shock generation system of claim 2, wherein the resonation simulator is configured to resonate between 12 Hz to 16 Hz.

14. The shock generation system of claim 2, wherein the at least one hinging mechanism includes an adjustable clevis that receives a clevis pin.

15. The shock generation system of claim 2, wherein the foundation structure comprises at least sixty thousand pounds of mass.

16. The shock generation system of claim 1 further comprising at least one removable weight.

17. The shock generation system of claim 1 further comprising at least one accelerometer that measures at least one aspect of the shock.

18. The shock generation system of claim 1, wherein the at least one swing arm comprises:
    a first swing arm; and
    a second swing arm.

19. A method of testing a target's response to a shock, comprising:
    mounting the target in a cage;
    elevating the cage to a height;
    causing the cage to fall from the height, thereby causing an impact shock to the cage;
    physically coupling the cage to a foundation structure in response to the cage falling from the height; and
    simulating a frequency response resulting from the impact shock.

20. The method of claim 19, wherein causing the cage to fall, further comprises causing the cage to fall at an angle, wherein falling at the angle causes the target to experience a rotational acceleration in response to the impact shock.

21. The method of claim 19, wherein causing the cage to fall, further comprises causing the cage to fall at an angle, wherein falling at the angle causes the target to experience a simulated athwartship acceleration in response to the impact shock.

22. The method of claim 19, wherein physically coupling the cage to the foundation further comprises using a locking assembly.

23. The method of claim 19, wherein simulating the frequency response further comprises utilizing at least one tunable coil mount.

24. The method of claim 19, wherein simulating the frequency response further comprises utilizing air cylinders.

25. The method of claim 19 further comprising measuring the impact shock.

26. The method of claim 19 further comprising calculating the height by dividing a desired impact velocity by twice the Earth's gravitational force.

27. The method of claim 19 further comprising mounting at least one additional weight onto the cage.

28. The method of claim 19 further comprising:
    compressing a resonation simulator prior to elevating the cage; and
    generating additional vertical velocity in response to the impact shock.

* * * * *